US009993410B2

(12) United States Patent
Haught et al.

(10) Patent No.: US 9,993,410 B2
(45) Date of Patent: Jun. 12, 2018

(54) REDUCTION IN CPC TASTE AVERSION BY REDUCING CPC ACTIVATION OF TRPA1, TPRV1, OR BOTH

(71) Applicant: The Procter & Gamble Company, Cincinnati, OH (US)

(72) Inventors: John Christian Haught, West Chester, OH (US); Koti Tatachar Sreekrishna, Mason, OH (US); Yakang Lin, Liberty Township, OH (US); Carrita Anne Hightower, Morrow, OH (US); Pierig Jean-Marie Lepont, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

(21) Appl. No.: 15/094,092

(22) Filed: Apr. 8, 2016

(65) Prior Publication Data

US 2016/0296445 A1 Oct. 13, 2016

Related U.S. Application Data

(60) Provisional application No. 62/145,383, filed on Apr. 9, 2015.

(51) Int. Cl.

| | |
|---|---|
| ***A61K 8/49*** | (2006.01) |
| ***A61K 8/37*** | (2006.01) |
| ***A61K 8/73*** | (2006.01) |
| ***A61K 8/60*** | (2006.01) |
| ***A61K 8/34*** | (2006.01) |
| ***A61K 8/44*** | (2006.01) |
| ***A61K 8/35*** | (2006.01) |
| ***A61K 8/41*** | (2006.01) |
| ***A61K 8/46*** | (2006.01) |
| ***A61Q 11/00*** | (2006.01) |
| ***G01N 33/68*** | (2006.01) |
| ***A61K 31/215*** | (2006.01) |
| ***A61K 31/40*** | (2006.01) |
| ***A61K 8/36*** | (2006.01) |
| ***A61K 8/365*** | (2006.01) |
| ***A61K 31/045*** | (2006.01) |
| ***A61K 31/121*** | (2006.01) |
| ***A61K 31/192*** | (2006.01) |
| ***A61K 31/222*** | (2006.01) |
| ***A61K 31/235*** | (2006.01) |
| ***A61K 31/4425*** | (2006.01) |
| ***A61K 33/30*** | (2006.01) |

(52) U.S. Cl.

CPC ............. *A61K 8/4926* (2013.01); *A61K 8/34* (2013.01); *A61K 8/35* (2013.01); *A61K 8/36* (2013.01); *A61K 8/361* (2013.01); *A61K 8/365* (2013.01); *A61K 8/37* (2013.01); *A61K 8/415* (2013.01); *A61K 8/445* (2013.01); *A61K 8/46* (2013.01); *A61K 8/602* (2013.01); *A61K 8/738* (2013.01); *A61K 31/045* (2013.01); *A61K 31/121* (2013.01); *A61K 31/192* (2013.01); *A61K 31/215* (2013.01); *A61K 31/222* (2013.01); *A61K 31/235* (2013.01); *A61K 31/40* (2013.01); *A61K 31/4425* (2013.01); *A61K 33/30* (2013.01); *A61Q 11/00* (2013.01); *G01N 33/6872* (2013.01); *A61K 2800/592* (2013.01); *G01N 2333/705* (2013.01); *G01N 2500/10* (2013.01)

(58) Field of Classification Search

CPC ..................................................... A61K 35/78

See application file for complete search history.

(56) References Cited

U.S. PATENT DOCUMENTS

| | | | |
|---|---|---|---|
| 2,946,725 | A | 7/1960 | Norris et al. |
| 3,070,510 | A | 12/1962 | Cooley et al. |
| 3,111,127 | A | 11/1963 | Jarboe |
| 3,535,421 | A | 10/1970 | Briner et al. |
| 3,538,230 | A | 11/1970 | Pader et al. |
| 3,678,154 | A | 7/1972 | Widder et al. |
| 3,862,307 | A | 1/1975 | Di Giulio |
| 3,917,613 | A | 11/1975 | Humbert et al. |
| 3,991,178 | A | 11/1976 | Humbert et al. |
| 4,029,759 | A | 6/1977 | Humbert et al. |
| 4,051,234 | A | 9/1977 | Gieske et al. |
| 4,070,496 | A | 1/1978 | Rowsell et al. |
| 4,136,163 | A | 1/1979 | Watson et al. |
| 4,150,052 | A | 4/1979 | Watson et al. |
| 4,153,679 | A | 5/1979 | Wilkinson et al. |
| 4,157,384 | A | 6/1979 | Watson et al. |
| 4,178,459 | A | 12/1979 | Rowsell et al. |
| 4,206,215 | A | 6/1980 | Bailey et al. |
| 4,230,688 | A | 10/1980 | Rowsell et al. |
| 4,340,583 | A | 7/1982 | Wason |
| 4,459,425 | A | 7/1984 | Amano et al. |
| 5,004,597 | A | 4/1991 | Majeti et al. |
| 5,180,577 | A | 1/1993 | Polefka et al. |
| 5,266,592 | A | 11/1993 | Grub et al. |

(Continued)

FOREIGN PATENT DOCUMENTS

| | | |
|---|---|---|
| EP | 310299 | 4/1989 |
| GB | 1315626 | 5/1973 |
| WO | WO8806850 | 9/1988 |
| WO | WO2005049553 | 6/2005 |
| WO | WO2006103401 | 10/2006 |

OTHER PUBLICATIONS

Molecular Devices, "FLIPR Calcium 5 Assay Kit." published May 5, 2010; 13 pages: https://mdc.custhelp.com/euf/assests/content/product_insert_D5001069[1].D.pdf.*

(Continued)

*Primary Examiner* — Walter E Webb

(74) *Attorney, Agent, or Firm* — Parker D. McCrary; James Ernest Oehlenschlager

(57) ABSTRACT

A method for screening compounds and compositions that reduce cetyl pyridinium chloride activation of TRPA1 receptor or TRPV1 receptor.

9 Claims, No Drawings

(56) References Cited

U.S. PATENT DOCUMENTS

| | | | |
|---|---|---|---|
| 5,281,410 A | 1/1994 | Lukacovic et al. | |
| 5,451,404 A | 9/1995 | Furman | |
| 5,578,293 A | 11/1996 | Prencipe et al. | |
| 5,589,160 A | 12/1996 | Rice | |
| 5,603,920 A | 2/1997 | Rice | |
| 5,608,119 A | 3/1997 | Amano et al. | |
| 5,651,958 A | 7/1997 | Rice | |
| 5,658,553 A | 8/1997 | Rice | |
| 5,703,123 A | 12/1997 | Pelzer et al. | |
| 5,716,601 A | 2/1998 | Rice | |
| 5,725,865 A | 3/1998 | Mane et al. | |
| 5,843,466 A | 12/1998 | Mane et al. | |
| 5,977,166 A | 11/1999 | Greenberg | |
| 6,365,215 B1 | 4/2002 | Grainger et al. | |
| 6,451,844 B1 | 9/2002 | Watkins et al. | |
| 6,592,884 B2 | 7/2003 | Hofmann et al. | |
| 6,884,903 B2 | 4/2005 | Lorenz et al. | |
| 6,956,139 B2 | 10/2005 | Green et al. | |
| 7,189,760 B2 | 3/2007 | Erman et al. | |
| 2005/0031717 A1* | 2/2005 | DeSimone ............ | A61K 31/00 424/760 |
| 2008/0153845 A1 | 6/2008 | Palmer et al. | |
| 2010/0278991 A1 | 11/2010 | Haught et al. | |
| 2012/0082628 A1 | 4/2012 | Haught et al. | |
| 2013/0315843 A1 | 11/2013 | Haught et al. | |
| 2014/0080842 A1 | 3/2014 | Krohn et al. | |

OTHER PUBLICATIONS

U.S. Appl. No. 15/669,576, filed Aug. 4, 2017, John Christian Haught et al.

Molecular Devices, "FLIPR Calcium 5 Assay Kit." published May 5, 2010; 13 pages: https:/ /mdc.custhelp.com/euf/assests/content/product_insert_D05001069[1].D. pdf.

Wolfram Miekisch, Jochen K. Schubert, Gabriele F.E. Noeldge-Schomburg, Clinica Chimica Acta, vol. 347, Issues 1-2, Sep. 2004, pp. 25-39.

Sandra Van Den Velde, Marc Quirynen, Paul Van Hee, Daniel Van Steenberghe, Journal of Chromatography B, vol. 853, Issues 1-2, Jun. 15, 2007, pp. 54-61.

Hongzhen Hu, Michael Bandell, Matt J Petrus, Michael X Zhu & Ardem Patapoutian, Nature Chemical Biology (2009), vol. 5, No. 3, pp. 183-190.

A. Saint-Eve, I. Déléris, G. Feron, D. Ibarra, E. Guichard, I. Souchon, Food Quality and Preference, vol. 21, Issue 8, Dec. 2010, pp. 1026-1033.

Johannes Snel, Maurits Burgering, Bart Smit, Wouter Noordman, Albert Tangerman, Edwin G. Winkel, Michiel Kleerebezem, Archives of Oral Biology, vol. 56, Issue 1, Jan. 2011, pp. 29-34.

PCT/US2016/026575 (P&G Case No. 13768M) International Search Report and Written Opinion dated Aug. 26, 2016.

Chung G et al: "Activation of transient receptor potential ankyrin 1 by eugenol", Neuroscience, vol. 261, Dec. 30, 2013 (Dec. 30, 2013),—Dec. 30, 2013 (Dec. 30, 2013), pp. 153-160, XP028605610, ISSN: 0306-4522, DOI: 10.1016/J.Neuroscience.2013.12.047.

Hillyard et al: "Chemosensory function of salt and water transport by the amphibian skin", Comparative Biochemistry and Physiology. Part A, Molecular and Integrative Physiology, Elsevier Science, New York, NY, US, vol. 148, No. 1, Jul. 20, 2007 (Jul. 20, 2007), pp. 44-54, XP022162545, ISSN: 1095-6433, DOI: 10.1016/J.CBPA.2006.12.025.

Lyall Vijay et al: "The mammalian amiloride-insensitive non-specific salt taste receptor is a vanilloid receptor-1 variant", The Journal of Physiology Jul. 1, 2004, vol. 558, no. Pt 1, Jul. 1, 2004 (Jul. 1, 2004), pp. 147-159, XP002758786, ISSN: 0022-3751.

J. Vriens et al: "Pharmacology of Vanilloid Transient Receptor Potential Cation Channels", Molecular Pharmacology, vol. 75, No. 6, Mar. 18, 2009 (Mar. 18, 2009), pp. 1262-1279, XP055200762, ISSN: 0026-895X, DOI: 10.1124/mo1.109.055624.

* cited by examiner

SEQUENCE LISTING

```
<160> NUMBER OF SEQ ID NOS: 2

<210> SEQ ID NO 1
<211> LENGTH: 2520
<212> TYPE: DNA
<213> ORGANISM: Homo sapiens

<400> SEQUENCE: 1

atgaagaaat ggagcagcac agacttgggg gcagctgcgg acccactcca aaaggacacc      60
tgcccagacc ccctggatgg agaccctaac tccaggccac ctccagccaa gccccagctc     120
tccacggcca agagccgcac ccggctcttt gggaagggtg actcggagga ggctttcccg     180
gtggattgcc ctcacgagga aggtgagctg gactcctgcc cgaccatcac agtcagccct     240
gttatcacca tccagaggcc aggagacggc cccaccggtg ccaggctgct gtcccaggac     300
tctgtcgccg ccagcaccga gaagaccctc aggctctatg atcgcaggag tatctttgaa     360
gccgttgctc agaataactg ccaggatctg gagagcctgc tgctcttcct gcagaagagc     420
aagaagcacc tcacagacaa cgagttcaaa gaccctgaga cagggaagac ctgtctgctg     480
aaagccatgc tcaacctgca cgacggacag aacaccacca tcccccctgct cctggagatc     540
gcgcggcaaa cggacagcct gaaggagctt gtcaacgcca gctacacgga cagctactac     600
aagggccaga cagcactgca catcgccatc gagagacgca acatggccct ggtgaccctc     660
ctggtggaga acggagcaga cgtccaggct gcggcccatg gggacttctt taagaaaacc     720
aaagggcggc ctggattcta cttcggtgaa ctgcccctgt ccctggccgc gtgcaccaac     780
cagctgggca tcgtgaagtt cctgctgcag aactcctggc agacggccga catcagcgcc     840
agggactcgg tgggcaacac ggtgctgcac gccctggtgg aggtggccga caacacggcc     900
gacaacacga agtttgtgac gagcatgtac aatgagattc tgatcctggg ggccaaactg     960
cacccgacgc tgaagctgga ggagctcacc aacaagaagg gaatgatgcc gctggctctg    1020
gcagctggga ccgggaagat cggggtcttg gcctatattc tccagcggga gatccaggag    1080
cccgagtgca ggcacctgtc caggaagttc accgagtggg cctacgggcc cgtgcactcc    1140
tcgctgtacg acctgtcctg catcgacacc tgcgagaaga actcggtgct ggaggtgatc    1200
gcctacagca gcagcgagac ccctaatcgc cacgacatgc tcttggtgga gccgctgaac    1260
cgactcctgc aggacaagtg ggacagattc gtcaagcgca tcttctactt caacttcctg    1320
gtctactgcc tgtacatgat catcttcacc atggctgcct actacaggcc cgtggatggc    1380
ttgcctccct ttaagatgga aaaaactgga gactatttcc gagttactgg agagatcctg    1440
tctgtgttag gaggagtcta cttctttttc cgagggattc agtatttcct gcagaggcgg    1500
ccgtcgatga agaccctgtt tgtggacagc tacagtgaga tgcttttctt tctgcagtca    1560
ctgttcatgc tggccaccgt ggtgctgtac ttcagccacc tcaaggagta tgtggcttcc    1620
atggtattct ccctggcctt gggctggacc aacatgctct actacacccg cggtttccag    1680
cagatgggca tctatgccgt catgatagag aagatgatcc tgagagacct gtgccgtttc    1740
atgtttgtct acatcgtctt cttgttcggg ttttccacag cggtggtgac gctgattgaa    1800
```

```
gacgggaaga atgactccct gccgtctgag tccacgtcgc acaggtggcg ggggcctgcc   1860

tgcaggcccc ccgatagctc ctacaacagc ctgtactcca cctgcctgga gctgttcaag   1920

ttcaccatcg gcatgggcga cctggagttc actgagaact atgacttcaa ggctgtcttc   1980

atcatcctgc tgctggccta tgtaattctc acctacatcc tcctgctcaa catgctcatc   2040

gccctcatgg gtgagactgt caacaagatc gcacaggaga gcaagaacat ctggaagctg   2100

cagagagcca tcaccatcct ggacacggag aagagcttcc ttaagtgcat gaggaaggcc   2160

ttccgctcag gcaagctgct gcaggtgggg tacacacctg atggcaagga cgactaccgg   2220

tggtgcttca gggtggacga ggtgaactgg accacctgga acaccaacgt gggcatcatc   2280

aacgaagacc cgggcaactg tgagggcgtc aagcgcaccc tgagcttctc cctgcggtca   2340

agcagagttt caggcagaca ctggaagaac tttgccctgg tccccctttt aagagaggca   2400

agtgctcgag ataggcagtc tgctcagccc gaggaagttt atctgcgaca gttttcaggg   2460

tctctgaagc cagaggacgc tgaggtcttc aagagtcctg ccgcttccgg ggagaagtga   2520
```

```
<210> SEQ ID NO 2
<211> LENGTH: 3360
<212> TYPE: DNA
<213> ORGANISM: Homo sapiens

<400> SEQUENCE: 2

atgaagtgca gcctgaggaa gatgtggcgc cctggagaaa agaaggagcc ccagggcgtt     60

gtctatgagg atgtgccgga cgacacggag gatttcaagg aatcgcttaa ggtggttttt    120

gaaggaagtg catatggatt acaaaacttt aataagcaaa agaaattaaa aacatgtgac    180

gatatggaca ccttcttctt gcattatgct gcagcagaag gccaaattga gctaatggag    240

aagatcacca gagattcctc tttggaagtg ctgcatgaaa tggatgatta tggaaatacc    300

cctctgcatt gtgctgtaga aaaaaaccaa attgaaagcg ttaagtttct tctcagcaga    360

ggagcaaacc caaacctccg aaacttcaac atgatggctc ctctccacat agctgtgcag    420

ggcatgaata atgaggtgat gaaggtcttg cttgagcata gaactattga tgttaatttg    480

gaaggagaaa atggaaacac agctgtgatc attgcgtgca ccacaaataa tagcgaagca    540

ttgcagattt tgcttaacaa aggagctaag ccatgtaaat caaataaatg ggatgtttc    600

cctattcacc aagctgcatt ttcaggttcc aaagaatgca tggaaataat actaaggttt    660

ggtgaagagc atgggtacag tagacagttg cacattaact ttatgaataa tgggaaagcc    720

acccctctcc acctggctgt gcaaaatggt gacttggaaa tgatcaaaat gtgcctggac    780

aatggtgcac aaatagaccc agtggagaag ggaaggtgca cagccattca ttttgctgcc    840

acccagggag ccactgagat tgttaaactg atgatatcgt cctattctgg tagcgtggat    900

attgttaaca caaccgatgg atgtcatgag accatgcttc acagagcttc attgtttgat    960

caccatgagc tagcagacta tttaatttca gtgggagcag atattaataa gatcgattct   1020

gaaggacgct ctccacttat attagcaact gcttctgcat cttggaatat tgtaaatttg   1080

ctactctcta aaggtgccca agtagacata aaagataatt ttggacgtaa ttttctgcat   1140

ttaactgtac agcaacctta tggattaaaa aatctgcgac ctgaatttat gcagatgcaa   1200

cagatcaaag agctggtaat ggatgaagac aacgatgggt gtactcctct acattatgca   1260

tgtagacagg ggggccctgg ttctgtaaat aacctacttg gctttaatgt gtccattcat   1320

tccaaaagca aagataagaa atcacctctg cattttgcag ccagttatgg gcgtatcaat   1380

acctgtcaga ggctcctaca agacataagt gatacgaggc ttctgaatga aggtgacctt   1440
```

-continued

```
catggaatga ctcctctcca tctggcagca aagaatggac atgataaagt agttcagctt   1500
cttctgaaaa aaggtgcatt gtttctcagt gaccacaatg gctggacagc tttgcatcat   1560
gcgtccatgg gcgggtacac tcagaccatg aaggtcattc ttgatactaa tttgaagtgc   1620
acagatcgct tggatgaaga cgggaacact gcacttcact ttgctgcaag ggaaggccac   1680
gccaaagccg ttgcgcttct tctgagccac aatgctgaca tagtcctgaa caagcagcag   1740
gcctcctttt tgcaccttgc acttcacaat aagaggaagg aggttgttct tacgatcatc   1800
aggagcaaaa gatgggatga atgtcttaag attttcagtc ataattctcc aggcaataaa   1860
tgtccaatta cagaaatgat agaataccte cctgaatgca tgaaggtact tttagatttc   1920
tgcatgttgc attccacaga agacaagtcc tgccgagact attatatcga gtataatttc   1980
aaatatcttc aatgtccatt agaattcacc aaaaaaacac ctacacagga tgttatatat   2040
gaaccgctta cagccctcaa cgcaatggta caaaataacc gcatagagct tctcaatcat   2100
cctgtgtgta aagaatattt actcatgaaa tggttggctt atggatttag agctcatatg   2160
atgaatttag gatcttactg tcttggtctc atacctatga ccattctcgt tgtcaatata   2220
aaaccaggaa tggctttcaa ctcaactggc atcatcaatg aaactagtga tcattcagaa   2280
atactagata ccacgaattc atatctaata aaaacttgta tgattttagt gtttttatca   2340
agtatatttg ggtattgcaa agaagcgggg caaattttcc aacagaaaag gaattatttt   2400
atggatataa gcaatgttct tgaatggatt atctacacga cgggcatcat ttttgtgctg   2460
cccttgtttg ttgaaatacc agctcatctg cagtggcaat gtggagcaat tgctgtttac   2520
ttctattgga tgaatttctt attgtatctt caaagatttg aaaattgtgg aatttttatt   2580
gttatgttgg aggtaatttt gaaaactttg ttgaggtcta cagttgtatt tatcttcctt   2640
cttctggctt ttggactcag cttttacatc ctcctgaatt tacaggatcc cttcagctct   2700
ccattgcttt ctataatcca gaccttcagc atgatgctag gagatatcaa ttatcgagag   2760
tccttcctag aaccatatct gagaaatgaa ttggcacatc cagttctgtc ctttgcacaa   2820
cttgtttcct tcacaatatt tgtcccaatt gtcctcatga atttacttat tggtttggca   2880
gttggcgaca ttgctgaggt ccagaaacat gcatcattga agaggatagc tatgcaggtg   2940
gaacttcata ccagcttaga gaagaagctg ccactttggt ttctacgcaa agtggatcag   3000
aaatccacca tcgtgtatcc caacaaaccc agatctggtg ggatgttatt ccatatattc   3060
tgttttttat tttgcactgg ggaaataaga caagaaatac caaatgctga taaatcttta   3120
gaaatggaaa tattaaagca gaaataccgg ctgaaggatc ttacttttct cctggaaaaa   3180
cagcatgagc tcattaaact gatcattcag aagatggaga tcatctctga gacagaggat   3240
gatgatagcc attgttcttt tcaagacagg tttaagaaag agcagatgga acaaaggaat   3300
agcagatgga atactgtgtt gagagcagtc aaggcaaaaa cacaccatct tgagccttag   3360
```

REDUCTION IN CPC TASTE AVERSION BY REDUCING CPC ACTIVATION OF TRPA1, TPRV1, OR BOTH

FIELD OF INVENTION

The present invention relates to CPC antagonists of TRPA1 and TRPV1 Receptor activation.

BACKGROUND OF THE INVENTION

As part of the definition of freshness in the mouth, more is explained by what is not present versus what is present. The area of breath mitigation has mostly been relegated to antibacterial actives and metal salts, which are usually delivered at the expense of taste. Breath malodor control at the point of brushing and shortly afterwards is a must have benefit for Oral Care products. The antibacterial agents reduce the malodors by reducing the amount of microbes present. The downside to these antibacterial agents is their lingering aftertaste. Breath malodor is primarily comprised of thiols and amines. The source of these odors depends upon the time of day, health of the individual, and the diet of the individual. Digestive odors and metabolic byproducts account for the halitosis at different times of the day (Archives of Oral Biology, Volume 56, Issue 1, January 2011, Pages 29-34; and Clinica Chimica Acta, Volume 347, Issues 1-2, September 2004, Pages 25-39; and Journal of Chromatography B, Volume 853, Issues 1-2, 15 Jun. 2007, Pages 54-61). The main culprits of halitosis (cysteine and methionine metabolic byproducts; isoprene; methylated hydrocarbons; butyric acid; 1-Propanol; and acetone) have off tastes associated with them. These off tasting molecules may also have trigeminal effects, in addition to the taste receptor interaction (Food Quality and Preference, Volume 21, Issue 8, December 2010, Pages 1026-1033).

In US Pub. No. 2005/0031717, they used activation of TRPV1 to modulate salty taste. At the levels of TRPV1 activation they used, they assign CPC as having no activity on TRPV1 and use CPC to modulate salt taste. In essence, they are using the negative properties of CPC to neutralize the negatives of high salt compositions. Thus, they would not have identified antagonists to CPC activation of TRPV1, as they were using CPC's properties as is, and wanted the CPC taste aversion to occur in order to offset salt perception.

In WO 8806850, they utilized cationic surfactants, such as CPC, and cationic amino acids to enhance the salty taste of foods and beverages. The enhancement was likely a result of the CPC's suppression of other tastes, causing the salty taste to be magnified.

While quaternary ammonium antimicrobials such as CPC have long been used in oral mouthrinses, there is still a need for additional formulations, which provide technology to mitigate the taste aversion negatives exhibited by these antimicrobials in some consumers, without compromising their effectiveness. The present invention relates to CPC containing compositions that provide increased consumer acceptance after use, due to the mitigation of the taste negatives.

SUMMARY OF THE INVENTION

A method of reducing cetyl pyridinium chloride (CPC) TRPA1 receptor or TRPV1 receptor activation is provided that comprises providing a cell that expresses at least one of TRPA1 receptor or TRPV1 receptor; adding CPC to the cell: adding at least one of a CPC TRPA1 receptor antagonist or CPC TRPV1 receptor antagonist; and measuring receptor activation of at least one of the TRPA1 receptor or TRPV1 receptor.

A method for screening compounds that reduce CPC TRPA1 or TRPV1 receptor activation by cetyl pyridinium chloride (CPC) is provide that comprises providing a cell that expresses at least one of a TRPA1 receptor or TRPV1 receptor; adding CPC to the cell; adding a test composition to the cell; measuring receptor activation of at least one of the TRPA1 receptor or TRPV1 receptor; and determining if TRPA1 receptor or TRPV1 receptor activation was reduced as compared to adding CPC to a cell without adding a test composition.

A personal care composition is provided that comprises CPC; and at least one of a CPC TRPA1 receptor antagonist or CPC TRPV1 receptor antagonist.

DETAILED DESCRIPTION OF THE INVENTION

It has now surprisingly been found that antagonists to cetyl pyridinium chloride (CPC) activation of TRPA1 and TRPV1 receptors provide a noticeable reduction in the taste aversion that occurs from the use of CPC in oral care compositions. Surprisingly, these antagonists are specific to the TPRA1 and TRPV1 receptors evoked sensations from CPC, as many of these antagonists do not block the standard agonists used on these receptors; such as, allyl isothiocyanate which is specific to TRPA1 receptors (does not activate TRPV1 receptors) and capsaicin which is specific to TRPV1 receptors (does not activate TRPA1 receptors). Additionally, as CPC acts across TRPA1 and TRPV1 receptors to generate a negative taste or lack of ability to taste, there exists an unmet need to provide antagonists to this taste signal generated by CPC's activation of TRPA1 or TRPV1 receptors.

CPC may alter taste perception during routine daily use of oral care compositions. This taste distortion is a result of CPC's activation of the TRPA1 and TRPV1 receptors. Therefore, antagonists to CPC's activation of these receptors would provide an improvement, in the after use experience on sweet and salty perceptions, when the antagonists are combined with CPC in an oral care composition. Other taste vectors influenced by TRPA1 and TRPV1 CPC receptor antagonists are sourness and bitterness.

The negative sensorial attributes of CPC's activation of TRPA1 and TRPV1 receptors, such as a lack of ability to taste foods after using a composition containing CPC or a metallic/astringent taste sensation, can be mitigated by combining CPC with one or more antagonists to CPC's activation of the TRPA1 or TRPV1 receptors. The antagonists may be delivered with CPC in the same composition or sequenced by delivering one first and then the other via different products or applications, for example in a regimen, such as by using a dentifrice followed by the use of a rinse. The present invention relates to personal care compositions and methods of using the personal care compositions, which in certain embodiments may comprise about 1.2% CPC or less, and which also include one or more antagonists to the TRPA1 or TRPV1 receptor.

Without being limited by theory, it is now believed that the negative sensations produced by CPC activation of TRPA1 or TRPV1 receptors can be reduced by the use of TRPA1 and TRPV1 antagonists specific to CPC activation.

| SEQ ID NO | Sequence |
|---|---|
| 1 | Human TRPV1 Receptor DNA sequence |
| 2 | Human TRPA1 Receptor DNA sequence |

A sequence listing that sets forth the nucleotide sequences for SEQ ID NO: 1 and 2 herein is being filed concurrently with the present application as an ASCII text file titled "13768M_TRPV1-TRPA1_ST25." The ASCII text file was created on 1 Mar. 2016 and is 8 Kbytes in size. In accordance with MPEP §605.08 and 37 CFR §1.52(e), the subject matter in the ASCII text file is incorporated herein by reference.

The term "TRPV1" or "TRPV1 receptor", as used herein, refers to the transient receptor potential vanilloid receptor 1; which is a ligand-gated, non-selective cation channel preferentially expressed on small-diameter sensory neurons and detects noxious as well as other substances. The TRPV1 receptor is provided as SEQ ID NO: 1.

The term "TRPV1 receptor agonist", as used herein, refers to any compound, which at a concentration of 1 mM gives a calcium flux count of at least 1000 counts or 20% above the background level of calcium present in the cell according to the FLIPR method, as discussed herein. The term "count" is defined as the change in fluorescence of the cell lines due to the influx of calcium across the cell membrane, which reacts with the calcium sensitive dye present within the cells.

The term "CPC TRPV1 receptor antagonist", as used herein, refers to any compound which at a concentration of 1 mM reduces TRPV1 receptor activation by 375 μM cetyl pyridinium chloride (CPC), as measured by calcium flux count of calcium present in the cell (in certain embodiments as measured by the FLIPR method), by at least 1000 counts or 20% below the activation of TRPV1 receptor by 375 μM cetyl pyridinium chloride (CPC). The term "count" is defined as the change in fluorescence of the cell lines due to the influx of calcium across the cell membrane, which reacts with the calcium sensitive dye present within the cells. The antagonistic effect may also be measured by looking at lower concentrations of the receptor agonist, such as CPC at 100 μM or lower. In certain embodiments a CPC TRPV1 receptor antagonist at a concentration of greater than 1 mM does not reduce TRPV1 receptor activation by 350 nM capsaicin, as measured by maximum calcium flux count of calcium present in the cell (in certain embodiments as measured by the FLIPR method), by at least 1000 counts or 20% below the activation of TRPV1 receptor by 350 nM capsaicin; meaning some antagonists have little to no effect on activation of TRPV1 by 350 nM capsaicin—making them CPC specific antagonists.

Wherein the CPC TRPV1 receptor antagonist may include one or more of the following: zinc acetate; 2-octenoic acid; 2-aminobenzoic acid naphthalene-2-yl ester; α-dimethylphenethyl butyrate; α-ionol; 4-(4-hydroxyphenyl)-butan-2-one; butyl isobutyrate; uteramine; β-ionol; 2-methoxycinnamaldehyde; 4-(4-methoxyphenyl)-2-butanone; β-ionone; N,N-dimethylanthranilic acid methyl ester; methyl 4-phenylbutyrate; or decyl acetate.

The term "TRPV1 receptor desensitizer", as used herein, refers to any compound, which shows agonist activity and causes a decrease in activation by a known TRPV1 receptor agonist. The following TRPV1 desensitizers may be utilized to desensitize the TRPV1 receptor to activation by CPC: β-cyclodextrin; tannic acid; isoeugenol; vanillyl ethyl ether; 4-allyl-2,6-dimethoxyphenol; 2-undecenal; myrtenol; 3-(1,3-benzodioxol-5-yl)-2-methylpropanal; L-borneol; p-tolylacetaldehyde; and dibasic sodium phosphate.

The term "TRPV1 receptor enhancer", as used herein, refers to any compound that boosts the calcium flux activity of an agonist that directly activates TRPV1 receptor, but does not directly activate TRPV1 receptor.

The term "TRPA1" or "TRPA1 receptor", as used herein, refers to the transient receptor potential cation channel, subfamily A, member 1, having a large cysteine-rich N-terminus that contains 18 predicted ankyrin repeats. TRPA1 is a ligand-gated, non-selective cation channel preferentially expressed on small diameter sensory neurons. The TRPA1 receptor is provided as SEQ ID NO: 2.

The term "TRPA1 receptor agonist", as used herein, refers to any compound, which at a concentration of 1 mM gives a calcium flux count of at least 1000 counts or 20% above the background level of calcium present in the cell according to the FLIPR method, as discussed herein. The term "count" is defined as the change in fluorescence of the cell lines due to the influx of calcium across the cell membrane, which reacts with the calcium sensitive dye present within the cells.

The term "CPC TRPA1 receptor antagonist", as used herein, refers to any compound which at a concentration of 1 mM reduces TRPA1 receptor activation by 375 μM cetyl pyridinium chloride (CPC), as measured by calcium flux count of calcium present in the cell (in certain embodiments as measured by the FLIPR method), by at least 1000 counts or 20% below the activation of TRPA1 receptor by 375 μM cetyl pyridinium chloride (CPC). The term "count" is defined as the change in fluorescence of the cell lines due to the influx of calcium across the cell membrane, which reacts with the calcium sensitive dye present within the cells. The antagonistic effect may also be measured by looking at lower concentrations of the receptor agonist, such as CPC at 100 μM or lower. In certain embodiments a CPC TRPA1 receptor antagonist at a concentration of greater than 1 mM does not reduce TRPA1 receptor activation by 50 μM allyl isothiocyanate, as measured by maximum calcium flux count of calcium present in the cell (in certain embodiments as measured by the FLIPR method), by at least 1000 counts or 20% below the activation of TRPA1 receptor by 50 μM allyl isothiocyanate; meaning some antagonists have little to no effect on activation of TRPA1 receptor by 50 μM allyl isothiocyanate—making them CPC specific antagonists.

Wherein the CPC TRPA1 receptor antagonist may include one or more of the following: eugenyl isovalerate; β-cyclodextrin; maltyl isobutyrate; tannic acid; manganese gluconate; p-mentha-8-thiol-3-one; myrtenol; OR manganese citrate.

The term "TRPA1 receptor enhancer", as used herein, refers to any compound that boosts the calcium flux activity of an agonist that directly activates TRPA1 receptor, but does not directly activate TRPA1 receptor.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated. All measurements referred to herein are made at 25° C. (i.e. room temperature), unless otherwise specified.

As used herein, the word "include," and its variants, are intended to be non-limiting, such that recitation of items in a list is not to the exclusion of other like items that may also be useful in the materials, compositions, devices, and methods of this invention.

As used herein, the word "or" when used as a connector of two or more elements is meant to include the elements individually and in combination; for example X or Y, means X or Y or both.

By "personal care composition" is meant a product which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, odor control or general aesthetics. Non-limiting examples of personal care compositions include hair coloring compositions; oral care compositions; after shave gels and creams; pre-shave preparations; shaving gels; creams, or foams; moisturizers and lotions; cough and cold compositions; leave-on skin lotions and creams; shampoos; conditioners; shower gels; bar soaps; toilet bars; antiperspirants; deodorants; depilatories; lipsticks; foundations; mascara; sunless tanners; and sunscreen lotions.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice; mouth rinse; mousse; foam; mouth spray; lozenge; chewable tablet; chewing gum; oral care strips, such as tooth whitening strips, breath freshening dissolvable strips, or sensitivity strips; floss and floss coating; or denture care or adhesive product. The oral care composition may also be incorporated onto strips or films for direct application or attachment to oral surfaces.

The term "dentifrice", as used herein, includes tooth or subgingival-paste, gel, powder, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "teeth", as used herein, refers to natural teeth as well as artificial teeth or dental prosthesis.

In addition to CPC TRPA1/TRPV1 receptor antagonists, the oral care compositions of the present invention may include one or more of the following components, such as metal salts, sweeteners, carrier materials, antimicrobial agents, bad breath reduction agents, bleaching agents separate from hydrogen peroxide, surfactants, flavors, anti-tartar agents, colorants, sensates, abrasive polishing materials, thickening materials, humectants, and other additives.

It is desirable that oral care compositions for use in cleaning and care of the oral cavity impart a fresh and clean feeling as this provides users with a signal of continuing freshness and cleanliness. In addition to the feeling of cleanliness, users also want to experience the benefits of oral care actives like anti-tartar agents, for example, through their oral care regimen. The ability to formulate a user acceptable oral care composition, however, raises challenges as many of the components used to impart a flavor can deliver a benefit. Conversely, components that are part of the base for the oral care composition can add unwanted tastes or sensations along with the targeted benefit for which they are added. Thus, formulating oral care compositions can be a balancing act between acceptable flavor and acceptable benefits.

Active and other ingredients useful with the present invention may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

A metal salt includes zinc salts, stannous salts, potassium salts, copper salts, alkali metal bicarbonate slats, and combinations thereof. Metal salts have a wide range of functions from antimicrobial agents to sensitivity agents or buffers. The oral care compositions of the present invention may contain metal salt in an amount from about 0.05% to about 11%, from about 0.5% to about 7%, or from about 1% to about 5%, by total weight of the composition.

It is common to have a fluoride compound present in dentifrices and other oral care compositions in an amount sufficient to give a fluoride ion concentration in the composition of from about 0.0025% to about 5.0% or from about 0.005% to about 2.0%, by weight of the oral care composition to provide anticaries effectiveness. A wide variety of fluoride ion-yielding materials can be employed as sources of soluble fluoride in the present invention. Representative fluoride ion sources include: stannous fluoride, sodium fluoride, potassium fluoride, amine fluoride, sodium monofluorophosphate, indium fluoride, amine fluorides such as Olaflur, and many others. Examples of suitable fluoride ion-yielding materials are found in U.S. Pat. No. 3,535,421 and U.S. Pat. No. 3,678,154.

Stannous salts include stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. Dentifrices containing stannous salts, particularly stannous fluoride and stannous chloride, are described in U.S. Pat. No. 5,004,597. Other descriptions of stannous salts are found in U.S. Pat. No. 5,578,293. and in U.S. Pat. No. 5,281,410. In addition to the stannous ion source, other ingredients used to stabilize the stannous may be included, such as the ingredients described in U.S. Pat. No. 5,004,597 and U.S. Pat. No. 5,578,293.

Zinc salts include zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

Potassium salts include potassium nitrate, potassium citrate, potassium oxalate, potassium bicarbonate, potassium acetate, potassium chloride, and combinations thereof.

In certain embodiments, the copper salt is selected from copper fluoride, copper chloride, copper iodide, copper chlorofluoride, copper actetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In a further embodiment, the copper salt is selected from copper gluconate, copper acetate, copper glycinate, and combinations thereof.

Alkali metal bicarbonate salts are soluble in water and unless stabilized, tend to release carbon dioxide in an aqueous system. Sodium bicarbonate, also known as baking soda, can be used as an alkali metal bicarbonate salt. The alkali metal bicarbonate salt also functions as a buffering agent. Because of the pH at which alkali metal bicarbonate salts buffer, the bicarbonate salt may be in a phase separate from the stannous ion source. In certain embodiments, the oral care compositions of the present invention may contain from about 0.5% to about 50%, from about 0.5% to about 30%, from about 2% to about 20%, or from about 5% to about 18% of an alkali metal bicarbonate salt, by weight of the oral care composition.

Some metal salts that may be used in the present invention, such as zinc chloride, zinc citrate, copper gluconate, and zinc gluconate, are also associated with an off taste described as dirty, dry, earthy, metallic, sour, bitter, and astringent. See, for example, an article by Hu, Hongzhen, et al in *Nature Chemical Biology* (2009), 5 (3), Pages 183-190, entitled: Zinc Activates Damage-Sensing TRPA1 Ion Channels.

Sweeteners include saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N—[N-[3-3-hydroxy-4-methoxyphenyl) propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and combinations thereof.

Rebiana is a steviolglycoside from Cargill Corp., Minneapolis, Minn., which is an extract from the leaves of the *Stevia rebaudiana* plant (hereinafter referred to as "Rebiana"). This is a crystalline diterpene glycoside, about 300× sweeter than sucrose. Examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable embodiments of the present invention, the combination of high-potency sweeteners comprises rebaudioside A in combination with rebaudioside B, rebaudioside C, rebaudioside F, rebaudioside F, stevioside, steviolbioside, dulcoside A. Sweeteners are generally included in an oral care composition at a level of about 0.0005% to about 2%, by total weight of the oral care composition.

Carrier materials include water, glycerin, sorbitol, polyethylene glycols having a molecular weight of less than about 50,000, propylene glycol and other edible polyhydric alcohols, ethanol, or combinations thereof. The oral care compositions of the present invention may include from about 5% to about 80%, by weight of the composition, of a carrier material. In certain embodiments, the compositions of the present invention may contain carrier materials in an amount of from about 10% to about 40%, by total weight of the oral care composition.

Antimicrobial agents include quaternary ammonium compounds. Those useful in the present invention include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Examples of pyridinium quaternary ammonium compounds include bis[4-(R-amino)-1-pyridinium] alkanes as disclosed in U.S. Pat. No. 4,206,215, and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725 and in U.S. Pat. No. 4,051,234. Examples of other antimicrobial agents include chlorhexidine, and flavor oils such as thymol. The compositions of the present invention may contain antimicrobial agents in an amount of from about 0.035% or more, from about 0.1% to about 1.5%, from about 0.045% to about 1.0%, or from about 0.05% to about 0.10%, by total weight of the oral care composition.

Bleaching agents include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. An example of a persulfate includes oxones. Some bleaching agents provide a cool burn sensation within an oral care composition, for example peroxides and percarbonates. The compositions of the present invention may contain bleaching agents in an amount of from about 0.01% to about 30%, from about 0.1% to about 10%, or from about 0.5% to about 5%, by total weight of the oral care composition.

Surfactants may include anionic surfactants such as organophosphate, which include alkyl phosphates. These surface active organophosphate agents have a strong affinity for enamel surfaces and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

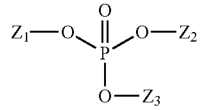

Some other organophosphate agents include alkyl or alkenyl phosphate esters represented by the following structure:

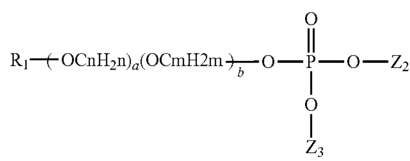

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a (OCmH2m)b-group. Examples of suitable agents include alkyl and alkyl (poly)alkoxy phosphates such as lauryl phosphate; PPGS ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N, N-dimethyl ammonio) acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these surfactants are soapy, bitter, chemical, or artificial.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation. Impurities may include dodecanol, dodecanal, benzaldehyde, and other TRPA1 or TRPV1 agonists.

Cationic surfactants useful in the present invention include derivatives of quaternary ammonium compounds having one long alkyl chain containing from about 8 to 18 carbon atoms such as lauryl trimethylammonium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No. 3,535,421. Certain cationic surfactants can also act as germicides in the oral care compositions disclosed herein.

Examples of some flavors and flavor components that may be used in oral care compositions are mint oils, wintergreen, clove bud oil, *cassia*, sage, parsley oil, marjoram, lemon, orange, propenyl guaethol, heliotropine, 4-cis-heptenal, diacetyl, methyl-ρ-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. Generally suitable flavoring ingredients are chemicals with structural features and functional groups that are less prone to redox reactions. These include derivatives of flavor chemicals that are saturated or contain stable aromatic rings or ester groups.

Flavors are generally present in an amount of from about 0.4% to about 5% or from about 1% to about 3%, by total weight of the oral care composition.

Anti-tartar agents include pyrophosphate salts as a source of pyrophosphate ion. The pyrophosphate salts useful in the present compositions include, for example, the mono-, di- and tetraalkali metal pyrophosphate salts and combinations thereof. Disodium dihydrogen pyrophosphate (Na2H2P2O7), sodium acid pyrophosphate, tetrasodium pyrophosphate (Na4P2O7), and tetrapotassium pyrophosphate (K4P2O7) in their unhydrated as well as hydrated forms are further species. In compositions of the present invention, the pyrophosphate salt may be present in one of three ways: predominately dissolved, predominately undissolved, or a combination of dissolved and undissolved pyrophosphate. The amount of pyrophosphate salt useful in making these compositions is any tartar control effective amount. In varying embodiments, the amount of pyrophosphate salt may be from about 1.5% to about 15%, from about 2% to about 10%, or about 3% to about 8%, by total weight of the oral care composition.

Examples of some colorants that may be used in oral care compositions include D&C Yellow No. 10, FD&C Blue No. 1, FD&C Red No. 40, D&C Red No. 33 and combinations thereof. In certain embodiments, the composition comprises colorant in an amount of from about 0.0001% to about 0.1% or from about 0.001% to about 0.01%, by weight of the oral care composition. Some colorants provide an unwanted taste, for example, D&C Red No. 33. The unwanted tastes often associated with this colorant are metallic, sharp, or chemical. Colorants are generally present in an amount of from about 0.001% to about 0.5%, by weight of the oral care composition.

Sensates may also be part of an oral care composition. Sensate molecules such as cooling, warming, and tingling agents are useful to deliver signals to the user. Sensates are generally present in an amount of from about 0.001% to about 0.8%, by weight of the oral care composition. The most well-known cooling sensate compound is menthol, particularly L-menthol, which is found naturally in peppermint oil notably of *Mentha arvensis* L and *Mentha viridis* L. Of the menthol isomers the L-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, for instance having disagreeable odor and taste described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there is no cooling effect for the other isomers. For example, d-neomenthol is reported to have a cooling threshold of about 25,000 ppb and 1-neomenthol about 3,000 ppb. [R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201].

Among synthetic coolants, many are derivatives of -or are structurally related to menthol, for example containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series, such as WS-5 (N-ethoxycarbonylmethyl-ρ-menthan-3-carboxamide), WS-12 (1R*,2S*)—N-(4-Methoxyphenyl)-5-methyl-2-(1-methylethyl)cyclohexanecarboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)p-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459; and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,703,123; 5,725,865; 5,843,466; 6,365,215; 6,451,844; and 6,884,903. Ketal derivatives are described, e.g., in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112 and phosphine oxides as reported in U.S. Pat. No. 4,070,496.

Some examples of warming sensates include ethanol; *capsicum*; nicotinate esters, such as benzyl nicotinate; polyhydric alcohols; *capsicum* powder; a *capsicum* tincture; *capsicum* extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the oral care composition.

Abrasive polishing material can be any material that does not excessively abrade dentin. The oral care compositions of the present invention may comprise abrasive polishing material in an amount of from about 6% to about 70% or from about 10% to about 50%, by weight of the oral care composition. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others, such as disclosed in U.S. Pat. No. 3,070,510. In certain embodiments, if the oral composition or particular phase comprises a polyphosphate having an average chain length of about 4 or more, calcium containing abrasives and alumina are not preferred abrasives.

Silica dental abrasives of various types are often used in oral care compositions due to their exceptional dental cleaning and polishing performance without unduly abrading tooth enamel or dentine. Silica abrasive polishing materials that may be used in the present invention, as well as other abrasives, generally have an average particle size ranging between about 0.1 μm to about 30 μm or from about 5 μm to about 15 μm. The abrasive can be precipitated silica or silica gels, such as the silica xerogels described in U.S. Pat. No. 3,538,230 and U.S. Pat. No. 3,862,307. Silica xerogels marketed under the trade name "Syloid" by the W.R. Grace & Company, Davison Chemical Division, Augusta, Ga. may be used. Also precipitated silica materials, such as those marketed by the J. M. Huber Corporation, Edison, N.J. under the trade name, "Zeodent", particularly the silica carrying the designation "Zeodent 119", may be used. The types of silica dental abrasives useful in the oral care compositions of the present invention are described in more detail in U.S. Pat. No. 4,340,583; and U.S. Pat. Nos. 5,589,160; 5,603,920; 5,651,958; 5,658,553; and 5,716,601.

Thickening material or binders may be used to provide a desirable consistency to the oral care compositions of the present invention. For example, when the oral care compositions are in the form of dentifrices, topical oral gels, mouthrinse, denture product, mouthsprays, lozenges, oral tablets, or chewing gums, the amount and type of the thickening material will depend upon the form of the product. Thickening materials include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening material to further improve texture. Thickening materials can be used in an amount from about 0.1% to about 15%, by weight of the oral care composition.

Humectants keep oral care compositions from hardening upon exposure to air and certain humectants can also impart desirable sweetness of flavor to dentifrice compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

EXAMPLES

Example 1

Assay for CPC Taste Distortion:

The assay included base taste solutions (sweet, salty, sour) and perceptual intensity evaluations by sensory panelists, as described below. The sensory panelists were 11 women all over the age of 18, and were used to generate all panel data used in the following EXAMPLES. Each panelist completed at least 120 hours of training on the definition and evaluation protocols of sensory attributes of a product/category. The training/evaluation approach is a Modified Spectrum™ method and conforms to ASTM guidelines on the Selection and Training of Sensory Panel Members. The base taste solutions (sweet, salty, sour—TABLE 1) were used to calibrate the panelists to taste intensity standards for each one of the base taste solutions (sweet, salty, sour) that they could use when evaluating the intensity of the samples and quantify the extent of CPC distortion versus taste recovery from the chemistry of invention.

Base taste solutions (sweet, salty, and sour) were prepared by dissolving (solutions were mixed until the particles were no longer visible when viewed at a distance of no more than 20 cm) identified ratios of specific taste raw material into filtered water (PuR filter) at room temperature (25° C.) to balance to 100%, as shown in TABLE 1.

TABLE 1

| | Concentration (wt %) | | |
|---|---|---|---|
| Base Taste | Low | Medium | High |
| Sweet | 5% sucrose | 10% sucrose | 16% sucrose |
| Salty | 0.35% sodium chloride | 0.50% sodium chloride | 0.70% sodium chloride |
| Sour | 0.08% Citric acid | 0.15% Citric acid | 0.20% Citric acid |
| Reference Value | 20 | 38 | 55 |

Additionally, as shown in TABLE 2, whole foods, having known and distinct tastes, were used to quantify the degree of CPC taste distortion. Those foods were: apple slices (peeled), tonic water, banana, pineapple juice, peppermint candy disc, and cream cheese.

TABLE 2

| Whole Food | Amount |
|---|---|
| Apple Slices (peeled) | 2.5 cm slice |
| Tonic Water | 30 ml |
| Banana | 2.5 cm slice |
| Pineapple Juice | 30 ml |
| Peppermint Candy Disc | 5 g disk |
| Cream Cheese | 20 g |

Reference Value

Using a 0 (lowest) to 60 (highest) intensity scale, the panelists correlated the taste of the base taste solution (low, medium, high) to an assigned reference value (20, 38, and 55 on a 60-point sensory scale) to establish baseline reference intensity values for each base taste solution. The panelists selected the reference values (20, 38, and 55 on a 60-point sensory scale). The panelists swished with filtered water to neutralize their mouths. The panelists self-determined the amount of water, duration, and frequency of pre-swishing needed to neutralize their mouths. Then, they swished with 10 ml of a concentration of sweet, salty, or sour for 30 seconds then expectorated. Immediately after expectoration, the panelist rated the intensity of the taste solution to align their taste experience with the solution's reference values. After each sample, the panelist waited for 20 minutes before evaluating the next taste concentration (low to medium and medium to high). This assessment approach was used for each of the nine solutions.

CPC Taste Distortion Testing:

Each panelist swished for 30 seconds with 10 ml of: a commercially available CPC mouthwash (Crest ProHealth Mouthwash—Procter & Gamble Co., Cincinnati, Ohio); a base taste solution (sweet, salty, and sour) from TABLE 1; or CPC mouthwash with TRPA1 or TRPV1 antagonists (rinses listed below in TABLE 7), then expectorated (prior to rating the sample CPC solutions each panelist swished with the tastant solutions and calibrated to the reference values (20, 38, 55). The panelists waited 20 minutes following expectoration before rinsing with 10 ml of a taste solution being sweet, salty, or sour at one of the defined concentrations. The taste intensity of the sample CPC solution was then rated on the 60 point scale. The 20 minute wash out period was observed between each sample. This approach evaluation was followed for each of nine base taste solutions within a single rinse variant testing session.

TABLE 3

BASELINE CPC TASTE DISTORTION

| | Concentration (wt %) | | |
|---|---|---|---|
| | Low | Medium | High |
| | Sweet 5% | Sweet 10% | Sweet 16% |
| Sweet Post CPC Rinse Value | 10 | 21 | 39 |
| | Salty 0.35% | Salty 0.50% | Salty 0.70% |
| Salty Post CPC Rinse Value | 11 | 16 | 24 |
| | Sour 0.08% | Sour 0.15% | Sour 0.20% |
| Sour Post CPC Rinse | 28 | 39 | 47 |
| Reference Value | 20 | 38 | 55 |

The data in TABLE 3 showed that sweet and salty were the most impacted sensory signals in a concentration dependent manner, from using a CPC rinse. For instance, the 10% base sweet solution had a reference value of 38 on the 0-60 scale when used by itself. Upon using the base sweet solution and then using the CPC rinse, the value of sweet dropped to 21. The 16% base sweet control solution had a reference value of 55 and upon using the CPC rinse, the base sweet solution was only perceived to be a 39 on that scale.

To understand the impact of CPC on taste within the context of foods, the whole foods were tested in a similar fashion to the taste solutions. The food items were prepared (preparation descriptions shown in TABLE 2) such that the portion sizes were consistent for each evaluation. The panelists were instructed to manipulate the food item in their mouths for 30 seconds. As shown in TABLE 4, the panel evaluated the intensity of sweet, salty, and sour for a food item before and after using a CPC rinse (Crest ProHealth Mouthwash). The panelists then rinsed their mouths with 10 mls of filtered water and waited 20 minutes before sampling the next food item.

TABLE 4

BASELINE CPC TASTE DISTORTION OF FOODS

| Food | Salty Taste | Salty Taste Post CPC Rinse | Sweet Taste | Sweet Taste Post CPC Rinse | Sour Taste | Sour Taste Post CPC Rinse |
|---|---|---|---|---|---|---|
| Apple | 0.2 | 0.7 | 19.6 | 14.3 | 9.2 | 10.2 |
| Tonic Water | 4.3 | 4.7 | 8.8 | 5.6 | 20.6 | 25.5 |
| Banana | 1.3 | 0 | 19.7 | 15.9 | 5.1 | 4.9 |
| Pineapple Juice | 1.3 | 2.2 | 21.7 | 23.1 | 18.7 | 20.6 |
| Peppermint Candy Disc | 2.6 | 2.3 | 32.2 | 31 | 2.9 | 2.4 |
| Cream Cheese | 16.2 | 13.8 | 5.8 | 6.8 | 15.3 | 12.7 |

Though the intended improvement for CPC taste distortion is when foods are eaten after using a CPC mouthwash, using whole foods to capture the degree of taste distortion was difficult, and most likely due to the complex nature and variability from each food type. Every other column in TABLE 4 above showed the impact of CPC on the sweet, sour, and salty taste of each of those foods. The difficulty may be related to foods being cooked for different amounts of time, and they have a mixture of sweet, salty, and sour; or fruits are not the same amount of ripeness from one to the next.

Example 2

TABLE 5 depicts the evaluation of antagonists to CPC activation of TRPA1 receptor. The activation of the TRPA1 receptor was done by combining the CPC with the TRPA1 expressing cell, in order to identify antagonists to activation of TRPA1 by CPC. HEK-293 (human embryonic kidney) cells stably transfected with human TRPA1 receptor (SEQ ID NO. 2) were grown in 15 ml growth medium [high glucose DMEM (Dulbecco's Modification of Eagle's Medium) supplemented with 10% FBS (fetal bovine serum)], 100 μg/ml Penicillin/streptomycin, 100 μg/ml G418] in a 75 $Cm^2$ flask for 3 days at 37° C. in a mammalian cell culture incubator set at 5% $CO_2$. Cells were detached with addition of 10 ml of PBS (phosphate buffered saline) by gentle hand shaking. Cells were transferred to a 50 ml tube and centrifuged at 850 rpm for 3 minutes to remove PBS. After centrifugation, a pellet of cells was formed in the bottom of the tube separating them from the supernatant solution. The supernatant was discarded and the cell pellet suspended in 1 ml of fresh growth medium to which 5 μl (12.5 μg) of Fluo-4 AM (Molecular Probes, Inc., Grand Island, N.Y.) calcium indicator was added and incubated for 30 min with gentle shaking. Fluo-4 AM is a fluorescent dye used for quantifying cellular $Ca^{2+}$ concentrations in the 100 nM to 1 microM range. At the end of the 30 minutes, 45 ml of assay buffer [1×HB SS (Hank's Balanced Salt Solution), 20 mM HEPES (4-(2-Hydroxyethyl)-1-piperazineethanesulfonic acid)] was added to wash cells and the resulting combination was then centrifuged at 850 rpm for 3 minutes to remove excess buffer and Fluo-4 AM calcium indicator;

following centrifugation the assay buffer was removed. The pellet cells were re-suspended in 10 ml assay buffer and 90 μl aliquots (~50,000 cells) per well delivered to a 96-well assay plate containing compounds (final concentration 1 mM for pure compounds, 0.04% for extracts) or buffer control and incubated at room temperature for 30 minutes. After 30 minutes, the plate was placed into a fluorometric imaging plate reader (FLIPR$^{TETRA}$ from Molecular Devices, Sunnyvale, Calif.) and basal fluorescence recorded (excitation wave length 488 nm and emission wave length 510 nm). The FLIPR assay is an accepted method for detecting changes in intracellular calcium concentration. Then 20 μl of the CPC (final concentration 100 uM) was added and fluorescence recorded. For determining the direct effect of test compounds on TRPA1 receptor, fluorescence was measured immediately after addition of each compound.

Compounds that reduced the CPC activation of the TRPA1 receptor by more than 20% were considered to be antagonistic to CPC activation of the TRPA1 receptor and thus good candidates for mitigating the off tasted associated with CPC activation of this receptor.

TABLE 5

(TRPA1 receptor antagonists to CPC activation of TRPA1)

| Compound | Cas No. | Ca count CPC (control) | Ca count AITC (Control) | Ca count Buffer (Control) | Ca count CPC TRPA1 Receptor Antagonist | % inhibition of CPC activation |
|---|---|---|---|---|---|---|
| n-propyl gallate | 121-79-9 | 5366 | 7875 | 101 | 1844 | 65.64 |
| beta-Cyclodextrin | 68168-23-0 | 5366 | 7875 | 101 | 2324 | 56.7 |
| Maltyl Isobutyrate | 65416-14-0 | 5366 | 7875 | 101 | 2882 | 46.3 |
| Tannic Acid | 1401-55-4 | 6798 | 7570 | 79 | 321 | 95.3 |
| Manganese Gluconate | 6485-39-8 | 6798 | 7570 | 79 | 2234 | 67.2 |
| P-mentha-8-thiol-3-one | 38462-22-5 | 6798 | 7570 | 79 | 3513 | 48.3 |
| Myrtenol | 19894-97-4 | 3152 | 5519 | 31 | 440 | 86.04 |
| Manganese Citrate | 10024-66-5 | 9532 | 9987 | 157 | 4553 | 52.2 |

The last column of TABLE 5 showed the level of antagonism to CPC activation of TRPA1 from the compounds tested. For instance, myrtenol had 86% inhibition of CPC activation of TRPA1 receptor.

TABLE 6 depicts the evaluation of antagonists to CPC activation of TRPV1 receptor. The activation of the TRPV1 receptor was done by combining the CPC with TRPV1 receptor expressing cell, as described in the methods. In order to identify antagonists of TRPV1 receptor activation by CPC, reduction in the CPC induced intracellular calcium ion ($Ca^{+2}$) level in the presence of antagonist was determined HEK-293 (human embryonic kidney) cells stably transfected with human TRPV1 receptor (SEQ ID NO. 1) were grown in 15 ml growth medium [high glucose DMEM (Dulbecco's Modification of Eagle's Medium) supplemented with 10% FBS (fetal bovine serum)], 100 μg/ml Penicillin/streptomycin, 100 μg/ml G418] in a 75 $Cm^2$ flask for 3 days at 33° C. in a mammalian cell culture incubator set at 5% $CO_2$. Cells were detached with addition of 10 ml of PBS (phosphate buffered saline) by hand shaking gently. Cells were transferred to a 50 ml tube and centrifuged at 850 rpm for 3 minutes to remove PBS. After centrifugation, a pellet of cells is formed in the bottom of the tube separating them from the supernatant solution. The supernatant was discarded and the cell pellet is suspended in 1 ml of fresh growth medium to which 5 μl (12.5 μg) of Fluo-4 AM (Molecular Probes, Inc.) calcium indicator was added and incubated for 30 min with gentle shaking. Fluo-4 AM is a fluorescent dye used for quantifying cellular $Ca^{2+}$ concentrations in the 100 nM to 1 mM range. At the end of the 30 minutes, 45 ml of assay buffer [1×HBSS (Hank's Balanced Salt Solution), 20 mM HEPES (4-(2-Hydroxyethyl)-1-piperazineethanesulfonic acid)] was added to wash cells and the resulting combination is then centrifuged at 850 rpm for 3 minutes to remove excess buffer and Fluo-4 AM calcium indicator; following centrifugation the assay buffer was removed. The pelleted cells were re-suspended in 10 ml assay buffer and 90 μl aliquots (50,000 cells) per well delivered to a 96-well assay plate containing compounds (final concentration 1 mM for pure compounds, 0.04% for extracts) or buffer control and incubated at room temperature for 30 minutes. After 30 minutes, the plate was placed into a fluorometric imaging plate reader (FLIPR$^{TETRA}$ from Molecular Devices) and basal fluorescence recorded (excitation wave length 488 nm and emission wave length 510 nm). The FLIPR assay is an accepted method for detecting changes in intracellular calcium concentration. Then 20 μl of the CPC (final concentration 100 uM) was added and fluorescence recorded. For determining the direct effect of test compounds on TRPV1 receptor, fluorescence was measured immediately after addition of each compound.

Compounds that reduced the CPC activation by more than 20% were considered to be antagonistic to CPC activation of this receptor and thus good candidates for mitigating the off tasted associated with CPC activation of this receptor.

TABLE 6

| (TRPV1 receptor antagonists to CPC activation of TRPV1) | | | | | | |
|---|---|---|---|---|---|---|
| Compound | Cas No. | Ca count CPC (control) | Ca count Capsaicin (Control) | Ca count Buffer (Control) | Ca count CPC TRPV1 Receptor Antagonist | % inhibition of CPC activation |
| Zinc Acetate | 557-34-6 | 13237 | 20285 | 225 | 1351 | 89.8 |
| 2-Octenoic Acid, Predominantly Trans | 1871-67-6 | 13237 | 20285 | 225 | 2878 | 78.26 |
| 2-Aminobenzoic Acid Naphthalen-2-Yl Ester | 63449-68-3 | 6760 | 16799 | 885 | 4172 | 38.3 |
| Alpha,Alpha-Dimethylphenethyl Butyrate | 10094-34-5 | 7751 | 12387 | 455 | 4246 | 45.22 |
| alpha-Ionol | 25312-34-9 | 7751 | 12387 | 455 | 2620 | 66.2 |
| 4-(4-Hydroxy-phenyl)-butan-2-one (Raspberry ketone) | 5471-51-2 | 3497 | 6233 | 2 | 1127 | 67.8 |
| Butyl Isobutyrate | 97-87-0 | 3497 | 6233 | 2 | 1504 | 57 |
| Uteramine | 51-67-2 | 3497 | 6233 | 2 | 1093 | 68.8 |
| beta-Ionol | 22029-76-1 | 3497 | 6233 | 2 | 1265 | 65.9 |
| 4-(4-Methoxyphenyl)-2-butanone | 104-20-1 | 3497 | 6233 | 2 | 1218 | 55.2 |
| Methyl 4-Phenylbutyrate | 2046-17-5 | 5223 | 9347 | 99 | 3469 | 43.6 |
| Decyl Acetate | 112-17-4 | 5223 | 9347 | 99 | 2079 | 60.2 |
| 3-Nonen-2-one | 14309-57-0 | 5223 | 9347 | 99 | 3470 | 43.6 |
| Magnesium sulfate | 7487-88-9 | 12250 | 18547 | 308 | 2199 | 88.1 |

The data from TABLE 6 showed the compounds that effectively inhibited CPC activation of TRPV1 receptor. For instance, beta-ionol inhibited CPC activation of TRPV1 by 65.9%.

Example 3

The rinses in TABLE 7 were prepared using conventional methods known to one of ordinary skill in the art.

Each expert panelist swished for 30 seconds with 10 ml of the control CPC rinse (no CPC receptor antagonists) or a Sample (1-A to 1-F having CPC TRPA1 or TRPV1 receptor antagonists), then expectorated. The panelists waited 20 minutes following expectoration before rinsing with 10 ml of a base taste solution being sweet, salty, or sour at one of the defined concentrations. The taste intensity of the sample CPC solution was then rated on the 60 point scale. The 20 minute wash out period was observed between each sample.

TABLE 7

| (Mouthwash Containing CPC Receptor Antagonists) | | | | | | | |
|---|---|---|---|---|---|---|---|
| | Control CPC | Samples | | | | | |
| Ingredient | Rinse | 1-A | 1-B | 1-C | 1-D | 1-E | 1-F |
| Superol Vegetable 99.7% Glycerine USP/FCC | 5.0% | 5.0% | 5.0% | 5.0% | 5.0% | 5.0% | 5.0% |
| Maltyl Isobutyrate | — | 0.11% | — | — | 0.05% | 0.05% | 0.05% |
| Raspberry Ketone | — | — | 0.012% | — | 0.012% | 0.012% | 0.012% |
| Methyl 4-Phenyl Butyrate | — | — | — | 0.012% | — | 0.012% | — |
| Delta Damascone | — | — | — | — | — | — | 0.012% |
| Propylene Glycol | 0.11% | 0.00% | 0.098% | 0.098% | 0.048% | 0.036% | 0.036% |
| Flavor | 0.09% | 0.09% | 0.09% | 0.09% | 0.09% | 0.09% | 0.09% |
| Poloxamer 407 | 0.06% | 0.06% | 0.06% | 0.06% | 0.06% | 0.06% | 0.06% |
| Methyl Paraben | 0.02% | 0.02% | 0.02% | 0.02% | 0.02% | 0.02% | 0.02% |
| Propyl Paraben | 0.005% | 0.005% | 0.005% | 0.005% | 0.005% | 0.005% | 0.005% |
| Sucralose NF | 0.01% | 0.01% | 0.01% | 0.01% | 0.01% | 0.01% | 0.01% |
| Sodium Saccharin | 0.01% | 0.01% | 0.01% | 0.01% | 0.01% | 0.01% | 0.01% |
| Cetyl Pyridinium Chloride | 0.74% | 0.74% | 0.74% | 0.74% | 0.74% | 0.74% | 0.74% |
| Dye FDL&C Blue #1 | 0.0005% | 0.0005% | 0.0005% | 0.0005% | 0.0005% | 0.0005% | 0.0005% |
| Water, Purified, USP | QS* | QS* | QS* | QS* | QS* | QS* | QS* |

*QS refers to the term quantum sufficit, meaning as much as suffices, where the remainder of the formula hole is filled with this substance This approach evaluation was followed for each of nine base taste solutions within a single rinse variant testing session. The numbers are the intensity ratings on the sensory 0-60 point scale.

TABLE 8

(CPC TRPA1 and TRPV1 Antagonists Improving Sweet Taste Perception)

| Sample | Low Conc. Sweet 5% | Med Conc. Sweet 10% | High Conc. Sweet 16% |
|---|---|---|---|
| Control Sweet Solution | 20 | 38 | 55 |
| Control CPC Rinse | 13 | 22 | 27 |
| Rinse 1-A | 14 | 41 | 45 |
| Rinse 1-B | 15 | 35 | 42 |
| Rinse 1-C | 21 | 38 | 48 |
| Rinse 1-D | 21 | 35 | 46 |
| Rinse 1-E | 15 | 36 | 50 |
| Rinse 1-F | 21 | 35 | 46 |

The control CPC rinse significantly reduced the sweet taste perception as compared to the control sweet solution. The impact of CPC on taste distortion was largest in the highest concentration of sweet (27 for control CPC rinse compared to 55 for the sweet solution). The addition of the CPC TRPA1 receptor antagonist, maltyl isobutyrate, in formulas 1-A, 1-D, 1-E, and 1-F showed a noticeable improvement in the taste aversion of CPC where the sweet perception was rated near that of the control value. The CPC TRPV1 antagonists, Raspberry ketone (Samples 1-B, 1-D, 1- and 1-F) and methyl-4-phenyl butyrate (Samples 1-C and 1-E), all improved the sweet taste perception; the greatest impact was when Maltyl Isobutyrate, Raspberry Ketone, and Methyl 4-Phenyl Butyrate (Sample 1-E) were combined. The addition of delta damascone, a long lasting taste character and a TRPA1 receptor and TRPV1 receptor enhancer, did not show an immediate impact (Sample 1-F), as compared to Sample 1-D (maltyl isobutyrate and raspberry ketone).

TABLE 9

(TRPA1 and TRPV1 CPC Antagonists Improving Salty Taste Perception)

| Sample | Low Conc. Salty 0.35% | Med. Conc. Salty 0.50% | High Conc. Salty 0.70% |
|---|---|---|---|
| Control Base Salty Solution | 20 | 38 | 55 |
| Control CPC Rinse | 11 | 18 | 24 |
| Rinse 1-A | 12 | 21 | 33 |
| Rinse 1-B | 15 | 23 | 34 |
| Rinse 1-C | 8 | 11 | 19 |
| Rinse 1-D | 8 | 16 | 20 |
| Rinse 1-E | 14 | 19 | 20 |
| Rinse 1-F | 8 | 16 | 20 |

The control CPC rinse significantly reduced the salty taste perception as compared to the Control Base Salty Solution. The impact of the control CPC rinse on salt taste distortion was approximately a 50% reduction in perception of the salt taste, regardless of the concentration of salt in the Control Salty Solution. The addition of the CPC TRPA1 receptor antagonist, maltyl isobutyrate, in Sample 1-A, showed an improvement in the taste aversion of CPC on salt perception at the higher concentration of salt tested, as compared to the Control CPC Rinse. The methyl-4-phenyl butyrate (Samples 1-C and 1-E) had less impact on improving the CPC taste aversion to salt perception. Adding Delta Damascone to Maltyl Isobutyrate and Raspberry Ketone (Sample 1-F) did not have as much impact as the individual components (Maltyl Isobutyrate, Sample 1-A; Raspberry Ketone, Sample 1-B). Both 1-A and 1-B showed an improvement over the control CPC rinse when looking at the highest salt concentration. The other samples did not show this, thus indicating some specificity of the chemistry towards salt and less specificity towards sweet.

TABLE 10

(CPC TRPA1 and TRPV1 Receptor Antagonists Improving Sour Taste Perception)

| | Low Conc. 0.08% Sour | Med. Conc. 0.15% Sour | High Conc. 0.20% Sour |
|---|---|---|---|
| Control Base Sour Solution | 20 | 38 | 55 |
| Control CPC Rinse | 30 | 43 | 44 |
| Rinse 1-A | 28 | 39 | 51 |
| Rinse 1-B | 23 | 37 | 40 |
| Rinse 1-C | 27 | 39 | 47 |
| Rinse 1-D | 24 | 37 | 46 |
| Rinse 1-E | 21 | 36 | 40 |
| Rinse 1-F | 24 | 37 | 46 |

The control CPC rinse increased the sour perception when compared to the 0.08% and 0.15% Control Base Sour Solution, while lowering sour perception at the high concentration level of the Control Sour Solution. The chemistry added in samples 1-A through 1-F, as compared to control CPC rinse, all kept the CPC from increasing the sour perception, at the Low Conc. of 0.08% and Med. Conc. of 0.15%, and maintained a sour perception near that of the control sour solution, at the High Conc. of 0.20%, thus preventing the taste distortion on this signal. This specific sour signal was citric acid and was perceived as a tart/astringent signal. Thus, increasing that signal was not a consumer desirable trait.

Example 4

CPC Taste Distortion Time Course Profile:

Panelists swished for 30 seconds with 10 ml of a base sweet solution (5% sucrose, 10% sucrose, and 16% sucrose), as defined in TABLE 1, for taste calibration. Following taste calibration the panelists swished with the control CPC rinse, and Samples 1-A, 1-B, and 1-C for 30 seconds. After using the rinse (control or sample), a panelist immediately swished with a 10% sweet taste solution, and rated the intensity of the solution for sweet using the 0-60 point descriptive analysis scale. The process of swishing and rating the solution was repeat every 5 minutes until a 30 min evaluation.

TABLE 11

Kinetic Study of Sweet Taste Response

| | Base Sweet Solution (10%) | Control CPC Rinse | Rinse 1-A (Maltyl Isobutyrate) | Rinse 1-B (Raspberry Ketone) | Rinse 1-C (Methyl-4-phenyl butyrate) |
|---|---|---|---|---|---|
| Immediate | 38 | 21.9 | 20.23 | 19.45 | 18.36 |
| 5 min | 38 | 29 | 28.36 | 30 | 31.18 |
| 10 min | 38 | 30.9 | 30.36 | 30.6 | 31.91 |
| 15 min | 38 | 33 | 32.73 | 32.4 | 33.59 |
| 20 min | 38 | 32 | 32.41 | 30.4 | 35.41 |
| 25 min | 38 | 31 | 35.18 | 33.3 | 35.14 |
| 30 min | 38 | 32.5 | 36.73 | 36.4 | 37.45 |

From TABLE 11, the data showed that CPC (control CPC rinse) continued to suppress the sweet taste over the course of 30 minutes, whereas Samples 1-A, 1-B and 1-C (having CPC TRPA1 and TRPV1 receptor antagonists) allowed the sweet taste to recover to normal 30 minutes after use, with the methyl-4-phenyl butyrate (Sample 1-C) allowing a more rapid rise in sweet taste recovery.

A. A method of reducing cetyl pyridinium chloride (CPC) TRPA1 receptor or TRPV1 receptor activation comprising:
  a. providing a cell that expresses at least one of TRPA1 receptor or TRPV1 receptor;
  b. adding CPC to the cell:
  c. adding at least one of a CPC TRPA1 receptor antagonist or CPC TRPV1 receptor antagonist;
  d. measuring receptor activation of at least one of the TRPA1 receptor or TRPV1 receptor.

B. The method according to paragraph A, wherein the receptor activation is measured by quantifying intracellular $Ca^{2+}$ levels as measured by FLIPR calcium flux, preferably wherein a fluorescent dye is used to quantify intracellular $Ca^{2+}$ levels.

C. The method according to paragraph B, wherein CPC TRPA1 receptor antagonist at a concentration of 1 mM reduces TRPA1 receptor activation by 375 μM cetyl pyridinium chloride (CPC), by at least 20% below the activation of TRPA1 receptor by 375 μM cetyl pyridinium chloride, preferably wherein the CPC TRPA1 receptor antagonist at a concentration of greater than 1 mM does not reduce TRPA1 receptor activation by 50 μM allyl isothiocyanate by at least 20% below the activation of TRPA1 receptor by 50 μM allyl isothiocyanate.

D. The method according to any of paragraphs A to C, wherein the CPC TRPA1 receptor antagonist comprises at least one of eugenyl isovalerate; b-cyclodextrin; maltyl isobutyrate; tannic acid; manganese gluconate; p-mentha-8-thiol-3-one; myrtenol; manganese citrate.

E. The method according to paragraph B or C, wherein CPC TRPV1 receptor antagonist at a concentration of 1 mM reduces TRPV1 receptor activation by 375 μM cetyl pyridinium chloride (CPC) by at least 1000 counts or 20% below the activation of TRPV1 receptor by 375 μM cetyl pyridinium chloride (CPC), preferably wherein the CPC TRPV1 receptor antagonist at a concentration of greater than 1 mM does not reduce TRPV1 receptor activation by 350 nM capsaicin by at least 20% below the activation of TRPV1 receptor by 350 nM capsaicin.

F. The method according to any of paragraphs A to E, wherein the CPC TRPV1 receptor antagonist comprises at least one of zinc acetate; 2-octenoic acid; 2-aminobenzoic acid naphthalene-2-yl ester; α-dimethylphenethyl butyrate; α-ionol; 4-(4-hydroxy-phenyl)-butan-2-one; butyl isobutyrate; uteramine; β-ionol; 2-methoxycinnamaldehyde; 4-(4-methoxyphenyl)-2-butanone; β-ionone; N,N-dimethylanthranilic acid methyl ester; methyl 4-phenylbutyrate; or decyl acetate.

G. A method for screening compounds that reduce CPC TRPA1 or TRPV1 receptor activation by cetyl pyridinium chloride (CPC) comprising:
  a. providing a cell that expresses at least one of a TRPA1 receptor or TRPV1 receptor;
  b. adding CPC to the cell;
  c. adding a test composition to the cell;
  d. measuring receptor activation of at least one of the TRPA1 receptor or TRPV1 receptor;
  e. determining if TRPA1 receptor or TRPV1 receptor activation was reduced as compared to adding CPC to a cell without adding a test composition.

H. The method according to paragraph G, wherein the receptor activation is measured by quantifying intracellular $Ca^{2+}$ levels as measured by FLIPR calcium flux, preferably wherein a fluorescent dye is used to quantify intracellular $Ca^{2+}$ levels.

I. A personal care composition comprising:
  a. CPC; and
  b. at least one of a CPC TRPA1 receptor antagonist or CPC TRPV1 receptor antagonist.

J. The personal care composition according to paragraph I, wherein the CPC TRPA1 receptor antagonist at a concentration of 1 mM reduces TRPA1 receptor activation by 375 cetyl pyridinium chloride (CPC), by at least 20% below the activation of TRPA1 receptor by 375 μM cetyl pyridinium chloride, preferably wherein the CPC TRPA1 receptor antagonist at a concentration of greater than 1 mM does not reduce TRPA1 receptor activation by 50 μM allyl isothiocyanate by at least 20% below the activation of TRPA1 receptor by 50 μM allyl isothiocyanate.

K. The personal care composition according to paragraph I or J, wherein CPC TRPV1 receptor antagonist at a concentration of 1 mM reduces TRPV1 receptor activation by 375 cetyl pyridinium chloride (CPC) by at least 1000 counts or 20% below the activation of TRPV1 receptor by 375 μM cetyl pyridinium chloride (CPC), preferably wherein the CPC TRPV1 receptor antagonist at a concentration of greater than 1 mM does not reduce TRPV1 receptor activation by 350 nM capsaicin by at least 20% below the activation of TRPV1 receptor by 350 nM capsaicin.

L. The personal care composition according to according to any of paragraphs I to K, wherein the CPC TRPA1 receptor antagonist comprises at least one of eugenyl isovalerate; b-cyclodextrin; maltyl isobutyrate; tannic acid; manganese gluconate; p-mentha-8-thiol-3-one; myrtenol; manganese citrate.

M. The personal care composition according to any of paragraphs I to L, wherein the CPC TRPV1 receptor antagonist comprises at least one of zinc acetate; 2-octenoic acid; 2-aminobenzoic acid naphthalene-2-yl ester; α-dimethylphenethyl butyrate; α-ionol; 4-(4-hydroxy-phenyl)-butan-2-one; butyl isobutyrate; uteramine; β-ionol; 2-methoxycinnamaldehyde; 4-(4-methoxyphenyl)-2-butanone; β-ionone; N,N-dimethylanthranilic acid methyl ester; methyl 4-phenylbutyrate; or decyl acetate.

N. The personal care composition according to any of paragraphs I to M, wherein the CPC TRPA1 receptor antagonist is maltyl isobutyrate and the CPC TRPV1 receptor antagonist is at least one of 4-(4-hydroxy-phenyl)-butan-2-one or methyl 4-phenyl butyrate.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing cetyl pyridinium chloride (CPC) TRPA1 receptor or TRPV1 receptor activation comprising:

a. providing a cell that expresses at least one of TRPA1 receptor or TRPV1 receptor;

b. adding CPC to the cell:

c. adding at least one of a CPC TRPA1 receptor antagonist or CPC TRPV1 receptor antagonist;

d. measuring receptor activation of at least one of the TRPA1 receptor or TRPV1 receptor;

wherein the receptor activation is measured by quantifying intracellular $Ca^{2+}$ levels as measured by FLIPR calcium flux; and wherein CPC TRPA1 receptor antagonist at a concentration of 1 mM reduces TRPA1 receptor activation by 375 μM cetyl pyridinium chloride (CPC), by at least 20% below the activation of TRPA1 receptor by 375 μM cetyl pyridinium chloride.

2. The method of claim 1, wherein a fluorescent dye is used to quantify intracellular $Ca^{2+}$ levels.

3. The method of claim 1, wherein the CPC TRPA1 receptor antagonist at a concentration of greater than 1 mM does not reduce TRPA1 receptor activation by 50 μM allyl isothiocyanate by at least 20% below the activation of TRPA1 receptor by 50 μM allyl isothiocyanate.

4. The method of claim 1, wherein the CPC TRPA1 receptor antagonist comprises at least one of eugenyl isovalerate; b-cyclodextrin; maltyl isobutyrate; tannic acid; manganese gluconate; p-mentha-8-thiol-3-one; myrtenol; manganese citrate.

5. The method of claim 1, wherein CPC TRPV1 receptor antagonist at a concentration of 1 mM reduces TRPV1 receptor activation by 375 cetyl pyridinium chloride (CPC) by at least 1000 counts or 20% below the activation of TRPV1 receptor by 375 μM cetyl pyridinium chloride (CPC).

6. The method of claim 5, wherein the CPC TRPV1 receptor antagonist at a concentration of greater than 1 mM does not reduce TRPV1 receptor activation by 350 nM capsaicin by at least 20% below the activation of TRPV1 receptor by 350 nM capsaicin.

7. The method of claim 1, wherein the CPC TRPV1 receptor antagonist comprises at least one of zinc acetate; 2-octenoic acid; 2-aminobenzoic acid naphthalene-2-yl ester; α-dimethylphenethyl butyrate; α-ionol; 4-(4-hydroxy-phenyl)-butan-2-one; butyl isobutyrate; uteramine; β-ionol; 2-methoxycinnamaldehyde; 4-(4-methoxyphenyl)-2-butanone; β-ionone; N,N-dimethylanthranilic acid methyl ester; methyl 4-phenylbutyrate; or decyl acetate.

8. A method of reducing cetyl pyridinium chloride (CPC) TRPA1 receptor or TRPV1 receptor activation comprising:

a. providing a cell that expresses at least one of TRPA1 receptor or TRPV1 receptor;

b. adding CPC to the cell:

c. adding at least one of a CPC TRPA1 receptor antagonist or CPC TRPV1 receptor antagonist;

d. measuring receptor activation of at least one of the TRPA1 receptor or TRPV1 receptor;

wherein the CPC TRPA1 receptor antagonist comprises at least one of eugenyl isovalerate; b-cyclodextrin; maltyl isobutyrate; tannic acid; manganese gluconate;

p-mentha-8-thiol-3-one; myrtenol; manganese citrate.

9. A method of reducing cetyl pyridinium chloride (CPC) TRPA1 receptor or TRPV1 receptor activation comprising:

a. providing a cell that expresses at least one of TRPA1 receptor or TRPV1 receptor;

b. adding CPC to the cell:

c. adding at least one of a CPC TRPA1 receptor antagonist or CPC TRPV1 receptor antagonist;

d. measuring receptor activation of at least one of the TRPA1 receptor or TRPV1 receptor;

wherein the CPC TRPV1 receptor antagonist comprises at least one of zinc acetate; 2-octenoic acid; 2-aminobenzoic acid naphthalene-2-yl ester; α-dimethylphenethyl butyrate; α-ionol; 4-(4-hydroxy-phenyl)-butan-2-one; butyl isobutyrate; uteramine; β-ionol; 2-methoxycinnamaldehyde; 4-(4-methoxyphenyl)-2-butanone; β-ionone; N,N-dimethylanthranilic acid methyl ester; methyl 4-phenylbutyrate; or decyl acetate.

* * * * *